US005780062A

United States Patent [19]
Frank et al.

[11] Patent Number: 5,780,062
[45] Date of Patent: Jul. 14, 1998

[54] SMALL PARTICLE FORMATION

[75] Inventors: Sylvan Frank, Columbus, Ohio; Jan-Erik Löfroth, Mölndal, Sweden; Levon Bostanian, Metairie, La.

[73] Assignee: The Ohio State University Research Foundation, Coloumbus, Ohio

[21] Appl. No.: 553,460

[22] PCT Filed: Nov. 3, 1995

[86] PCT No.: PCT/SE95/01302

§ 371 Date: Nov. 27, 1996

§ 102(e) Date: Nov. 27, 1996

[87] PCT Pub. No.: WO96/14833

PCT Pub. Date: May 23, 1996

[30] Foreign Application Priority Data

Nov. 9, 1994 [SE] Sweden .................................. 9403846

[51] Int. Cl.⁶ .................................................... A61K 9/16
[52] U.S. Cl. ................................................ 424/501; 424/489
[58] Field of Search ...................................... 424/501, 489

[56] References Cited

U.S. PATENT DOCUMENTS

| | | | |
|---|---|---|---|
| 4,606,940 | 8/1986 | Frank et al. | 427/213.32 |
| 4,826,689 | 5/1989 | Violanto et al. | 424/489 |

FOREIGN PATENT DOCUMENTS

| | | |
|---|---|---|
| 0169618 | 1/1986 | European Pat. Off. |
| 0486959 | 5/1992 | European Pat. Off. |
| 2-49720 | 2/1990 | Japan . |
| 2122085 | 1/1984 | United Kingdom . |
| 8603676 | 7/1986 | WIPO . |
| 9015593 | 12/1990 | WIPO . |

OTHER PUBLICATIONS

Derwent Abstract Accession No. 95–06706, Bostonian et al., "Characterization of Small Particles of Probucol." Pharm. Res. 11, No. 10, Suppl., S326, 1994.

Lofroth et al. "Interactions between surfactants and polymers. I:HPMC." Prog. Colloid Polym. Sci., 84:73–77 (1991).

M. L. Fishman et al., "Interactions of Aqueous Poly (N–vinylpyrrolidone) with Sodium Dodecyl Sulfate." J. Phys. Chem., vol. 75, No. 20, 1971, p. 3135.

Fincher, J.H. "Particle Size of Drugs and Its Relationship to Absorption and Activity" J. Pharm. Sciences 57(11): 1825–1835, 1968.

Shaw, D.J. "Introduction to Colloid and Surface Chemistry" 3rd Ed. Butterworths Pub. pp. 1–18, 1980.

Derwent Abstract Accession No. 93–14549, Bostonian et al. "Formation of Small Particles of a Relativly Insoluble Drug." Pharm. Res. 9, No. 10, Suppl., S224, 1992.

Primary Examiner—Joseph L. Schofer
Assistant Examiner—Wu C. Cheng
Attorney, Agent, or Firm—White & Case L.L.P.

[57] ABSTRACT

The present invention is concerned with the formation of small particles of organic compounds by precipitating said organic compounds in an aqueous medium containing polymer/amphiphile complexes. The process is preferably used to prepare a readily soluble pharmaceutically active compound.

7 Claims, No Drawings

SMALL PARTICLE FORMATION

The present invention is concerned with the formation of small particles of organic compounds upon precipitation when a solution of such an organic compound in a water-miscible solvent is added to an aqueous medium containing polymer and an amphiphilic compound (surfactant or lipid) at a concentration at which polymer/amphiphile complexes are formed. At said concentrations, the system is a solution below the critical concentration at which free micelles are formed. Upon addition of the organic compound, the compound interacts with the polymer/amphiphile complexes, thus increasing their hydrophobicity and leading to precipitation of organic compound/polymer/amphiphile aggregates.

According to the present invention, a small particle refers to a particle size of less than 2 μm.

The object of the invention is to provide a process for the formation of small particles of organic compounds, especially pharmaceutically active compounds, where such process does not involve emulsification or water-immisicible solvents.

The process is preferably used to prepare a readily soluble pharmaceutically active compound.

BACKGROUND OF THE INVENTION

From a pharmaceutical point of view, the smaller the particle size of a relatively insoluble drug, the grater is its rate of solution and as a rule, the greater is its bioavailability (J. H. Fincher, J. Pharm. Sci., 57, 1825 (1968)). To this end, small particles are conventionally formed by mechanical subdivision of bulk matter or by aggregation of small molecules or ions (D. J. Shaw, "Introduction to Colloid and Surface Chemistry", 3rd Ed., Butterworths, London, 1980, Chapter 1).

Studies of polymer/amphiphile systems in aqueous media have shown that interactions of polymers with charged amphiphiles occur in different stages. Ionic polymers and charged amphiphiles of opposite charge precipitate accordingly by electrostatic interactions. On the other hand, interactions between non-ionic polymers and amphiphiles occur in three stages. In the most dilute solutions, very little physical biding occurs. At concentrations of amphiphile higher than the critical micelle concentration, true micelles form. However, between these two concentrations, complexation or binding of polymer to amphiphile occurs (M. L. Fishman and F. R. Eirich, J. Phys. Chem., 75(20), 3135–40 (1971)). Small polymer/amphiphile aggregates or submicelles are thus formed. The presence of the amphiphile introduces an effective attraction between different polymer molecules since the formed aggregates could involve more than one polymer molecule. This attraction, together with the binding of the amphiphile to the polymer would lead to an increase in the hydrophobicity of the polymer. If the aggregate is sufficiently hydrophobic it will precipitate. The addition of a polar water-soluble compound (e.g. NaCl) to a polymer/amphiphile system will further enhance the precipitation of the polymer/amphiphile aggregates because there will be an increased difference in polarity between the solvent and the polymer/amphiphile aggregates and because the polar compound will tend to decrease the number of water molecules available for the hydration of the polymer/amphiphile aggregates. Also, precipitation occurs on increasing the temperature of systems containing polymers for which solubility is inversely related to temperature, such as cellulosic derivatives. The cloud point of hydroxypropylmethylcellulose (HPMC) has been shown to be lowered by addition of amphiphiles, the effect being more pronounced in the presence of salt (J. E. Löfroth, L. Johansson, A. C. Norman, and K. Wettström, Progr. Colloid. Polym. Sci., 84, 73–77 (1991)).

On the other hand, if a hydrophobic compound is added, it will tend to interact with the polymer/amphiphile aggregates, thus increasing the hydrophobicity of these polymer/amphiphile aggregates and facilitating their precipitation.

SUMMARY OF THE INVENTION

A method has now been found which surprisingly involves the formation of small particles, the growth of which is limited by the adsorption and/or concentration of polymer/amphiphile aggregates at the solid/liquid interface.

Thus, the invention concerns a process for preparing small particles comprising an organic compound, the solubility of which is greater in a water-miscible first solvent than in a second solvent which is aqueous, which process comprises the following steps:

(i) dissolving said organic compound in the water-miscible first solvent, (ii) preparing a solution of a polymer and an amphiphile in the aqueous second solvent and in which second solvent the organic compound is substantially insoluble whereby a polymer/amphiphile complex is formed, and (iii) mixing the solutions from steps (i) and (ii) so as to cause precipitation of an aggregate comprising the organic compound and the polymer/amphiphile complex.

The new method for the formation of small particles of an organic compound comprises:

1) Dissolving said compound in a first solvent which is water-miscible and in which said compound is soluble.

2) Preparing a solution of polymer and amphiphile in a second solvent which is aqueous and in which the compound for which small particles are desired is more or less insoluble, preferably at concentrations below the critical concentration at which free micelles begin to form. The concentrations of polymer and amphiphile are such that they interact, but the critical micelle concentration of the amphiphile is not reached. The hydrophobicity of the polymer is thus increased to a desired degree at which no precipitation occurs. Precipitation of the polymer could also be prevented by temperature control in the cases where solubility of the polymer is a function of temperature.

3) Mixing the solutions from steps (1) and (2) while stirring. The organic compound interacts with the polymer/amphiphile complexes, thus increasing their hydrophobicity, and precipitation of drug/polymer/amphiphile aggregates occurs.

4) The formed particles are then separated, preferably by flocculation and collected by suitable means.

An organic compound for use in the process of this invention is any organic chemical entity whose solubility decreases from one solvent to another. This organic compound might be a pharmaceutically active compound from various groups such as, but not limited to: antihyperlipidemics, antimicrobials, e.g. sulfadiazine; nonsteroidal anti-inflammatories, e.g., indomethacin; antihypercholesteremic agents, e.g., probucol; and steroidal compounds, e.g., dexamethasone. Or the organic compound might be from the group used as adjuvants or excipients in pharmaceutical preparations and cosmetics, such as, but not limited to, preservatives, e.g., propylparaben.

The first solvent according to the present invention is a solvent or mixture of solvents in which the organic compound of interest is relatively soluble and which is miscible with the second solvent. Examples of such solvents include, but are not limited to: methanol, ethanol, isopropanol, acetone, dimethylformamide, and acetonitrile.

The second solvent according to the present invention is water or an aqueous solution containing one or more of various additives, such as, but not limited to:

1. polymers, such as dextrans; polyethylene glucols; polyvinylpyrrolidone; cellulosic derivatives, e.g., methylcellulose and hydroxypropylmethylcellulose; gelatin; and carrageenan.
2. salts, such as monovalent ions, e.g., sodium chloride; divalent ions, e.g., sodium sulfate and calcium chloride; and trivalent ions, e.g., aluminum chloride.
3. surfactants such as nonionics, e.g., sorbitan fatty acid esters and their polyoxyethylene derivatives; anionics, e.g., sodium dodecylsulfate; and cationics, e.g., cetyltrimethylammonium bromide.
4. viscosity enhancing agents, such as, hydrophilic colloids, e.g., gelatin, acacia and tragacanth.
5. cosolvents, such as glycerol, propylene glycol, methanol, ethanol and isopropanol.

A polymer according to the invention, the solution of which is prepared in the second solvent, is meant to be a wide variety of organic chemical entities of relatively high molecular weight, such as, but not limited to:

1. vinyl derivatives, e.g., polyvinylpyrrolidone.
2. cellulose derivatives, e.g., methylcellulose and hydroxypropylmethylcellulose.
3. polyethylene glycols, e.g., polyethylene glycol 6,000 and polyethylene glycol 10,000.

An amphiphile according to the invention is a compound, the molecules of which consist of two parts, one of which is hydrophilic and the other of which is hydrophobic in nature. These compounds include, but are not limited to:

1. nonionics, e.g., cholesterol, lecithin, sorbitan fatty acid esters and their polyoxyethylene derivatives.
2. anionics, such as, alkylsulfates, e.g., sodium dodecylsulfate; and bile salts, e.g., sodium cholate and sodium taurocholate.
3. cationics, e.g., cetyltrimethylammonium bromide and benzalkonium chloride.

The concentration of the organic compound in the first solvent can be as low as 0.01% by weight and as high as, but not limited to, the saturation concentration of the organic compound in the first solvent, including concentrations which form supersaturated solutions within the range of temperatures up to the boiling point of the first solvent.

The concentration of the polymer can be ranging from 0.01% to 50% by weight in the second solvent, preferably 0.01% to 10%.

The concentration of the amphiphile can be ranging from 0.001% to 50% by weight in the second solvent, preferably 0.001% to 5%.

Flocculation can be achieved by various modes, such as 1. addition of an electrolyte, such as, but not limited to, sodium sulfate, sodium phosphate and potassium phosphate.
2. temperature change.
3. addition of a high molecular weight polymer (bridging flocculation).

Collection of the small particles can be achieved by various methods, such as, but not limited to:

1. centrifugation and ultracentrifugation.
2. filtration.
3. reverse osmosis followed by evaporation.
4. evaporation of the solvent by heating and/or vacuum.

5. freeze-drying.
6. spray-drying.
7. fluidized-bed drying.
8. any combination of the above.

DETAILED DESCRIPTION OF THE INVENTION

According to one embodiment of the invention, the process comprises the following steps:

1) Dissolving a pharmaceutically active compound, such as an antihyperlipidemic agent, in a first solvent which is water-miscible;
2) Dissolving polyvinylpyrrolidone and sodium dodecylsulfate in a second solvent which is aqueous such as water and in which the active compound is more or less insoluble. The concentrations of both polyvinylpyrrolidone and sodium dodecylsulfate are such that the system is below the critical concentration at which free micelles form and precipitation of the polymer/amphiphile complex has not occurred.
3) Adding the solution obtained from step (1) to that prepared in step (2) while keeping the latter under constant agitation. Precipitation occurs and results in a suspension of drug/polymer/amphiphile small particles.
4) The small particles thus obtained are flocculated by the addition of an aqueous solution of an electrolyte, such as potassium phosphate.
5) The suspension is centrifuged and washed twice with water, centrifuged, redispersed in water and then freeze-dried.

The process of forming small particles according to the invention is illustrated by the following example:

EXAMPLE

A solution consisting of 1 g of probucol (a lipid lowering drug) and 12 ml of absolute ethanol was added to a solution consisting of 2 g polyvinylpyrrolidone (M. W. 360.000), 0.1 g sodium dodecylsulfate and 50 ml water while stirring at 1.200 rpm with a magnetic stirrer. This procedure resulted in a white suspension of small particles comprising probucol. The small particles were then flocculated by adding a potassium phosphate solution. The flocculated small particles were separated by centrifugation, washed twice with water, redispersed by sonication and then freeze-dried. The process was monitored by observation of samples in the optical microscope. The final freeze-dried product was observed by electron microscopy; agglomerates of small particles of less than 2 μm were observed.

We claim:

1. A process for preparing small particles comprising an organic compound, the solubility of which is greater in a water-miscible first solvent than in a second solvent which is aqueous, which process comprises the following steps:
   (i) dissolving said organic compound in the water-miscible first solvent,
   (ii) preparing a solution of polymer and an amphiphile in the aqueous second solvent and in which second solvent the organic compound is substantially insoluble whereby a polymer/amphiphile complex is formed, and
   (iii) mixing the solutions from steps (i) and (ii) so as to cause precipitation of an aggregate comprising the organic compound and the polymer/amphiphile complex.

2. A process according to claim 1, wherein the polymer and amphiphile present in the solution produced according to step (ii) are at concentrations below the critical concentration at which free micelles begin to form.

3. A process according to claim 1 wherein flocculation of the precipitated aggregate is achieved by the addition of an electrolyte, and thereafter separation of the aggregate is achieved by means of centrifugation so that aggregates of less than 2 μm in size are separated out.

4. A process according to any one of the preceding claims wherein the polymer and the amphiphile are mixed in solution, interact and are precipitated by the addition of a hydrophobic organic compound.

5. A process according to claim 4 wherein the compound is pharmaceutically active.

6. A process as claimed in claim 5 wherein the pharmaceutically active compound is an antihyperlipidemic agent.

7. A process according to claim 6 in which the polymer is a pharmaceutically acceptable adjuvant.

* * * * *